United States Patent
Yagita

(10) Patent No.: US 6,911,653 B2
(45) Date of Patent: Jun. 28, 2005

(54) INSPECTING METHOD AND APPARATUS FOR FOREIGN MATTER

(75) Inventor: Kiyoshi Yagita, Tokyo (JP)

(73) Assignee: Scan Technology Co., Ltd., Tokyo (JP)

( * ) Notice: Subject to any disclaimer, the term of this patent is extended or adjusted under 35 U.S.C. 154(b) by 367 days.

(21) Appl. No.: 10/251,259

(22) Filed: Sep. 19, 2002

(65) Prior Publication Data

US 2003/0201384 A1 Oct. 30, 2003

(30) Foreign Application Priority Data

Apr. 26, 2002 (JP) ........................ 2002-125969

(51) Int. Cl.$^7$ ............................................. G01N 21/59
(52) U.S. Cl. ................ 250/341.1; 250/343; 250/339.06
(58) Field of Search .......................... 250/341.1, 223 B, 250/432 R, 339.06, 343, 338.5, 341.8; 382/141, 142

(56) References Cited

U.S. PATENT DOCUMENTS

| | | | | |
|---|---|---|---|---|
| 4,197,457 A | * | 4/1980 | Cheo ........................ | 250/338.1 |
| 4,241,256 A | | 12/1980 | Tagaya et al. .......... | 250/223 B |
| 4,367,405 A | | 1/1983 | Ford ....................... | 250/223 B |
| 4,402,612 A | | 9/1983 | Alexander et al. .......... | 356/427 |
| 4,914,289 A | | 4/1990 | Nguyen et al. ......... | 250/223 B |
| 4,943,713 A | * | 7/1990 | Yoshida .................. | 250/223 B |
| 5,072,108 A | | 12/1991 | Ishikawa ................ | 250/223 B |
| 5,256,871 A | | 10/1993 | Baldwin ................. | 250/223 B |
| 5,444,237 A | | 8/1995 | Takizawa ................ | 250/223 B |
| 5,486,692 A | | 1/1996 | Baldwin .................. | 250/223 B |
| 5,489,692 A | | 2/1996 | Hirschmann et al. ....... | 548/519 |
| 5,495,330 A | | 2/1996 | Champaneri et al. ....... | 356/240 |
| 5,536,935 A | | 7/1996 | Klotzsch et al. ............ | 250/223 |
| 5,591,899 A | | 1/1997 | Griesbeck .................. | 73/41 B |
| 5,661,294 A | | 8/1997 | Buchmann et al. ..... | 250/223 B |
| 5,748,305 A | * | 5/1998 | Shimono et al. .......... | 356/237.2 |
| 5,864,395 A | | 1/1999 | Laurberg .................. | 356/239.6 |
| 5,905,595 A | | 5/1999 | Minami ..................... | 359/618 |
| 5,926,268 A | | 7/1999 | Bonewitz et al. ........... | 356/240 |
| 6,067,155 A | | 5/2000 | Ringlien ..................... | 356/240 |
| 6,175,107 B1 | | 1/2001 | Juvinall .................. | 250/223 B |
| 6,275,603 B1 | * | 8/2001 | Cronshaw et al. .......... | 382/142 |
| 6,737,651 B1 | * | 5/2004 | Lendl ......................... | 250/343 |
| 2002/0154809 A1 | * | 10/2002 | Yamagishi et al. ......... | 382/142 |
| 2003/0142299 A1 | | 7/2003 | Kwirandt ................. | 356/239.5 |
| 2003/0214649 A1 | | 11/2003 | Yagita ..................... | 356/239.5 |

FOREIGN PATENT DOCUMENTS

JP     2002-221498     8/2002

* cited by examiner

*Primary Examiner*—David Porta
*Assistant Examiner*—Faye Polyzos
(74) *Attorney, Agent, or Firm*—Ladas & Parry LLP

(57) ABSTRACT

An object being inspected that contains a liquid product is irradiated with light from a first side face thereof and with light given with a tilt from either side of a second side face opposite to the first side face with respect to the object being inspected, transmitted light and reflected light from the object being inspected are received by imaging means provided at the second side face, and an image signal from the imaging means is processed, whereby a foreign matter got entered the liquid product is detected based on the image processing. Consequently, it is possible to provide inspecting method and apparatus for a foreign matter for use in a production line for manufacturing liquid products, such as drinks and liquid drugs, which can detect, at a high speed in a reliable manner, whether a foreign matter has entered a liquid inside a container, such as a bottle or a PET bottle, and a foreign matter got entered a colored bottle or PET bottle or a colored liquid as well.

10 Claims, 6 Drawing Sheets

INSPECTING METHOD AND APPARATUS FOR FOREIGN MATTER

BACKGROUND OF THE INVENTION

1. Field of the Invention

The present invention relates to an inspecting method and an apparatus for a foreign matter for detecting a foreign matter(impurities) got entered a liquid product(including a fluid product), such as drinks and liquid drugs, and more particularly to inspecting method and apparatus for a foreign matter capable of detecting, at high speed and accuracy, a foreign matter got entered a liquid product inside a container of such a complicated shape that makes inspection difficult by improving a light irradiating optical system used for inspection.

2. Description of the Related Background Art

Adoption of the HACCP (Hazard Analysis Critical Control Point) system to the Food Sanitation Law and enforcement of the PL(Product Liability) Law in recent years have been making it mandatory to further ensure the product safety by forestalling a hazard, such as microbial contamination and entrance of foreign matters like metal, fabrics, hair, etc., that could occur in any stage from manufacturing/processing of products, such as food and drugs, to consumption by end consumers through storage/distribution of the products.

HACCP is a hazard analysis and critical control point system established in the United States and is highly evaluated across the world as a sanitary control system method. The HACCP system is a science-based sanitary control system in which product safety is addressed throughout the manufacturing procedure so that preventive measures in the manufacturing procedure are emphasized in contrast to a conventional sanitary control system in which inspection of final products is emphasized. The HACCP system includes two sections: hazard analysis(HA) and critical control point (CCP), and it further ensures the product safety by forestalling an occurrence of a hazard in the manufacturing procedure without overlooking any possibility by (1) checking/analyzing a hazard, such as microbial contamination, that could occur in any stage from manufacturing/processing of food to consumption by end consumers through storage/distribution of the products and setting critical control points to prevent the hazard, (2) setting the criteria of control and constantly monitoring whether the critical limit is being met by checking the records of control, and (3) managing and controlling hazards of other natures with a pre-requisite program(PP).

In a conventional mass-production line of a manufacturing factory, workers detect foreign matters got entered liquids filled in containers by visual inspection. Because such visual inspection is tedious and time-consuming, it is conducted on spot-check basis that one in every certain number of containers is picked up and inspected. Hence, there is a problem that it is by no means reliable inspection conducted for each individual product.

In the case of a method on one hundred percent inspection basis by deploying inspectors along the production line, the inspectors(workers) are able to detect relatively large foreign matters by visual inspection, but they fail in detecting minute foreign matters, which raises a problem that the detection is less accurate. More importantly, the ability of visual inspection of the inspectors is no longer comparable to an increasing speed of the production line, and it is true that the inspection efficiency is becoming poor.

As a method for detecting a foreign matter got entered a container filled with a liquid other than the visual inspection, the container may be pictured from the outside by an inspection camera, so that the presence or absence of non-conformity is detected based on the resulting image information.

FIG. 1 is a view showing an example of such a method. According to this method, a light source 100 irradiates a PET bottle 101, namely an object being inspected, from the side face thereof, and transmitted light from the PET bottle 101 is received by a CCD sensor 102 serving as an imaging means. Then, a light reception signal from the CCD sensor 102 is subjected to image processing by a data processing apparatus (not shown), whereby a foreign matter got entered a liquid product inside the PET bottle 101 is detected.

With the inspecting apparatus arranged as above, the CCD sensor 102 receives transmitted light from the PET bottle 101, and the image processing apparatus, such as a personal computer, processes the light reception signal from the CCD sensor 102, so that a foreign matter got entered the liquid product inside the PET bottle 101 is detected. In this case, there is considerable interference on the surface of the container, such as reflection of scattered light from the outside and a bright line, which is resulted from a complicated shape of the container or the materials of the container, and irregularities on the surface of the container and the contour line of the container cause a change in intensity in the same way as a foreign matter does. For this reason, an image information(raw data) as shown in FIG. 2 is obtained at the CCD sensor 102. Therefore, even if the image processing apparatus processes the image information and converts the same into a binary image as shown in FIG. 3, it is difficult to precisely identify a foreign matter alone on the image thus obtained. In other words, besides a problem that the reliability is lowered, there is a problem that irregular reflection on the container is erroneously detected as a foreign matter and manufacturing yield is reduced.

There is known another detecting method, according to which a foreign matter is detected by inducing motions in a liquid by rotating a container filled with the liquid, and by obtaining the trail of associated movements of a foreign matter as the image information. This method, however, is feasible on the precondition that the container is of a simple shape having no irregularities on the surface, and therefore, it has a drawback that containers subjected to inspection are limited. Also, because an inspection time per container is too long, this method has a problem that it is not suitable for use in a high-speed mass-production line for drinks or liquid drugs.

Further, a method of masking a portion that need not be inspected, such as a mold line of the container, by editing a pictured image with software may be proposed. However, the products are generally flown into an imaging area of the inspecting apparatus provided to the production line at various rotational angles. Hence, when the containers are pictured as images, the position of the irregularities on the surface of the container varies from image to image, which poses a problem that it is virtually impossible to set a fixed masking area.

Additionally, the conventional inspecting apparatus is not able to detect a foreign matter by an optical method or irradiation of laser beams when a colored translucent PET bottle or bottle is filled with a transparent liquid, or when a transparent PET bottle or bottle is filled with a colored liquid, such as coffee, juice or cola. A foreign matter may be detected with X-rays when the container is opaque or translucent. However, the X-rays per se have ill effects on the human body; moreover, a large-scale and fairly expensive apparatus needs to be installed.

For this reason, the inspection of a bottle or a PET bottle for a foreign matter has not been conducted at all once a colored liquid product is filled therein. However, in order to attain the perfection of the products, there has been a need to conduct the inspection of bottles or PET bottles for foreign matters in a reliable manner whether the liquids are transparent or colored.

SUMMARY OF THE INVENTION

The present invention is devised in view of the foregoing, and has an object to provide an inspecting method and an apparatus for a foreign matter for use in a production line for manufacturing liquid products, such as drinks and liquid drugs, which can detect, at a high speed in a reliable manner, whether a foreign matter has entered a liquid inside a container, such as a bottle or a PET bottle, and a foreign matter in a colored bottle or PET bottle or in a colored liquid as well.

The present invention relates to an inspecting method for a foreign matter, and the object of the invention is achieved by performing: a step of irradiating an object being inspected that contains a liquid product with light from a first side face thereof; a step of irradiating the object being inspected with light given with a tilt from either side of a second side face opposite to the first side face with respect to the object being inspected; a step of receiving transmitted light and reflected light from the object being inspected by imaging means provided at the second side face; a step of processing an image signal from the imaging means; and
  a step of detecting a foreign matter got entered the liquid product based on the image processing.

The object of the present invention is achieved more effectively by arranging in such a manner that: an angle of the tilt is 30° to 60° with respect to a normal to the first side face of the object being inspected; light irradiated from the first side face and light irradiated from either side of the second side face are infrared light having a wavelength of 750 to 1000 nm; or the infrared light is irradiated at power in a range from 0.7 mW to 100 W both inclusive.

The present invention also relates to an inspecting apparatus for a foreign matter, and the object of the invention is achieved by including: a first light source for irradiating an object being inspected that contains a liquid product with light from a first side face thereof; a plurality of second light sources for irradiating the object being inspected with light given with a tilt from either side of a second side face opposite to the first side face with respect to the object being inspected; imaging means, provided at the second side face, for receiving transmitted light and reflected light from the object being inspected; and image processing and judging means for detecting a foreign matter got entered the liquid product by processing an image signal from the imaging means.

The object of the present invention is achieved more effectively by arranging in such a manner that: the imaging means is a CCD sensor; the number of the plurality of second light sources is two; the first light source and the second light sources are infrared light having a wavelength of 750 to 1000 nm; or the first light source and the second light sources have power in a range from 0.7 mW to 100 W both inclusive.

BRIEF DESCRIPTION OF THE DRAWINGS

The above and other objects will become more apparent when a preferred embodiment of the invention is considered in connection with the drawings, in which.

DETAILED DESCRIPTION OF THE PREFERRED EMBODIMENTS

Figure 1:
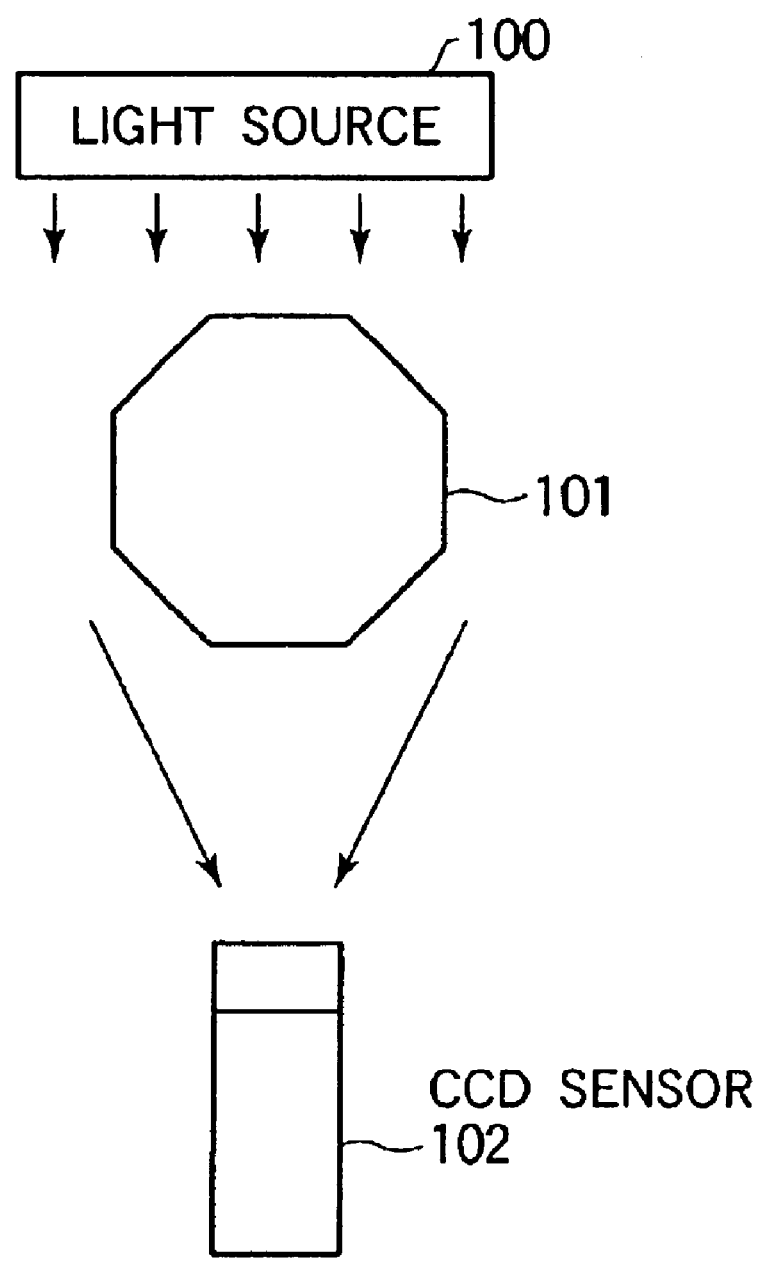
FIG. 1 is a view showing an example of an arrangement of a conventional inspecting apparatus for a foreign matter.
Figure 2:
FIG. 2 is a view showing an image as an example of an image obtained by the conventional inspecting apparatus for a foreign matter.
Figure 3:
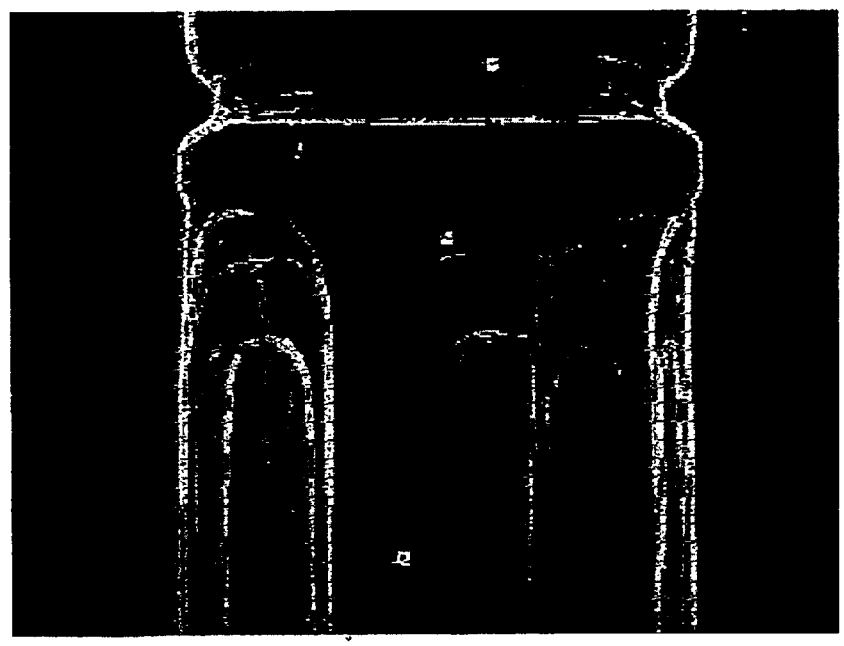
FIG. 3 is a view showing an image as an example of an image obtained by the conventional inspecting apparatus for a foreign matter.

According to the present invention, in a production line for manufacturing a liquid product(including a fluid product), such as drinks and liquid drugs, a CCD sensor serving as an imaging means receives transmitted light and reflected light of light irradiated to an object being inspected from a light source, whereby whether a foreign matter(either suspend or deposited), such as metal, fabrics, hair or dust, has entered a container, such as a bottle or a PET bottle, is detected at a high speed in a reliable manner. Further, even when the liquid product is a colored liquid, such as coffee, cola, juice or milk, or even when a translucent or colored bottle or PET bottle is filled with a transparent liquid product, such as mineral water, it is possible to detect a foreign matter got entered the liquid at a high speed in a reliable manner without stopping the production line by irradiating certain infrared light. In other words, according to the present invention, a foreign matter entering during the manufacturing/processing procedure of the product, including, for example, a raw material foreign matter that cannot be removed by inspection of the raw materials, an environmental foreign matter that would possibly enter upon placement on the production line, and a manufacturing machine foreign matter entering from the manufacturing machine itself during the manufacturing, is detected in a reliable manner in the final stage and a non-conforming product containing a foreign matter is removed in a reliable manner. Hence, even when the container is of a complicated shape, it is possible to identify only a foreign matter got entered a liquid filled in the container from a change in intensity caused by the container itself in a reliable manner without being adversely affected by reflection of scattered light from the outside or a bright line, which facilitates the image processing of a foreign matter pictured by the imaging means.

The following description will describe a preferred embodiment of the invention with reference to the accompanying drawings.

In the present invention, an object being inspected(for example, a PET bottle or a bottle) containing a liquid product is irradiated with light(for example, infrared light or a beam of laser) from a first side face thereof, and with light(for example, infrared light, a beam of laser) given with a tilt from a second side face opposite to the first side face with respect to the object being inspected. Transmitted light and reflected light from the object being inspected are received simultaneously by an imaging means(for example, a CCD sensor) provided at the second side face end, and an image signal from the imaging means is processed, whereby a foreign matter got entered the liquid product is detected based on the image processing. In other words, according to the present invention, not only light is irradiated to the object being inspected from the first side face thereof, but also light given with a tilt is irradiated from the second side face opposite to the first side face with respect to the object being inspected, and both the transmitted light and the reflected light from the object being inspected are received by the imaging means provided at the second side face end. By receiving the transmitted light and the reflected light from the objected being inspected simultaneously in this manner, it is possible to remove the contour or the shape of the object being inspected from an image pictured by the imaging means, thereby making it possible to obtain an image of a foreign matter alone. Consequently, the foreign matter can be detected at a high speed in a reliable manner.

Also, when an image is pictured at the CCD sensor by irradiating certain infrared light(wavelength: 750 to 1000 nm, power: 0.7 mW to 100 W) from a light source, it is possible to detect a foreign matter in a reliable manner even when the liquid product is a colored liquid, such as coffee, cola, juice or milk, or even when a translucent or colored bottle or PET bottle is filled with a transparent liquid product such as mineral water.

Figure 4:
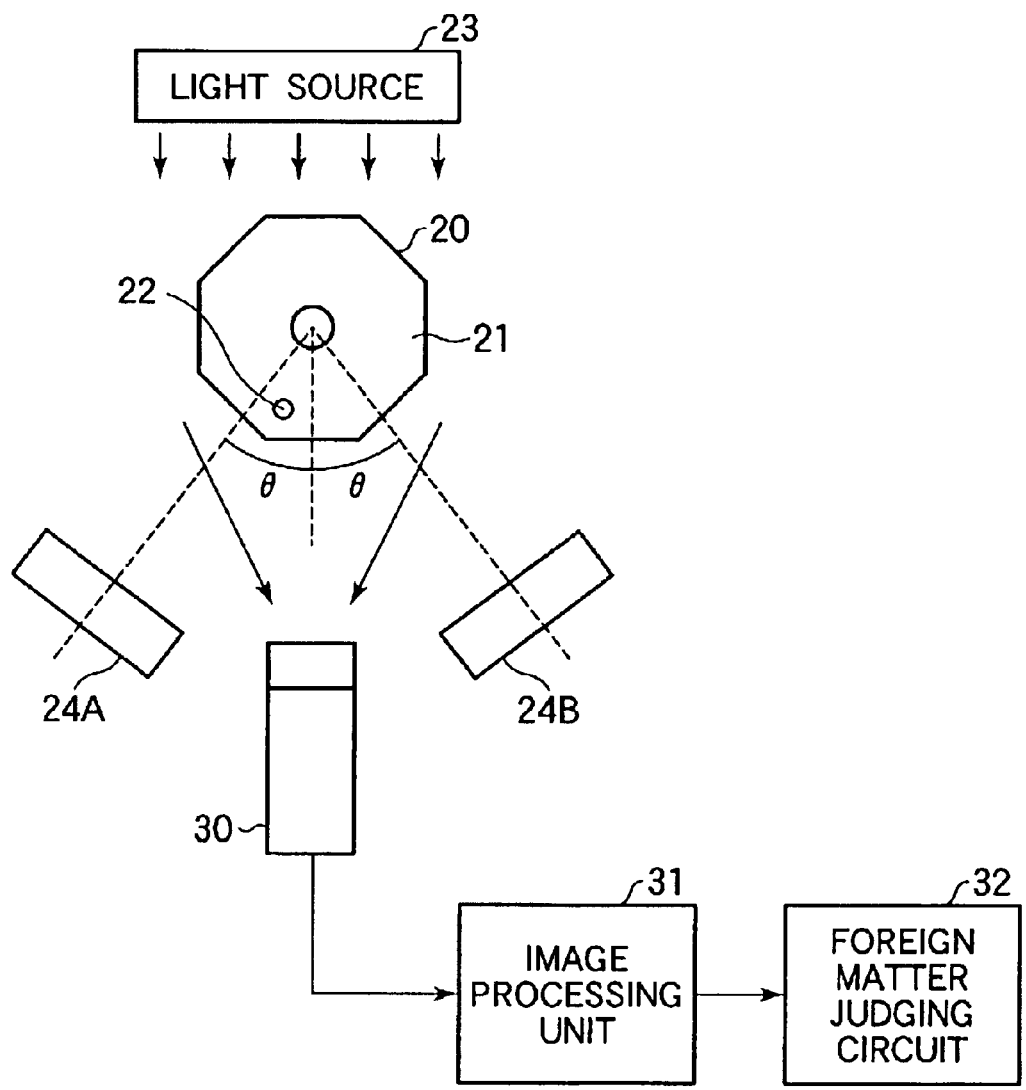
FIG. 4 is a view showing an arrangement according to one embodiment of the present invention.

FIG. 4 is a view showing an example of an inspecting apparatus for a foreign matter to achieve the inspecting method described above. Assume that a PET bottle 20 as an object being inspected is filled with a liquid(for example, water, drops, etc.) 21, and a foreign matter 22 has entered the liquid 21. A light source 23 is provided at a first side face(the upper side of the drawing) of the PET bottle 20, and a pair of light sources 24A and 24B are provided with a tilt(at an angle θ with respect to the normal) at a second side face (either lower side of the drawing) opposite to the first side face with respect to the PET bottle 20. The light sources 24A and 24B have an equal quantity of light, and are provided under the same conditions. A CCD(Charge-Coupled Device) sensor 30 serving as an imaging means is provided at the second side face(the lower side of the drawing) of the PET bottle 20. The CCD sensor 30 is connected to an image processing unit 31 for effecting the image processing on an image signal derived from an image pictured by the CCD sensor 30, and to a foreign matter judging circuit 32 for judging the presence of a foreign matter according to the image processing. Herein, the angle θ may be 30° to 60° and is preferably about 45°.

Figure 5:
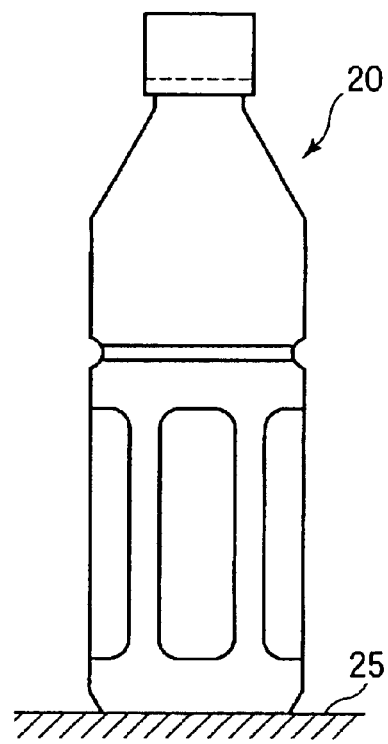
FIG. 5 is a view showing a detection state of a PET bottle in the present invention.
Figure 6A:
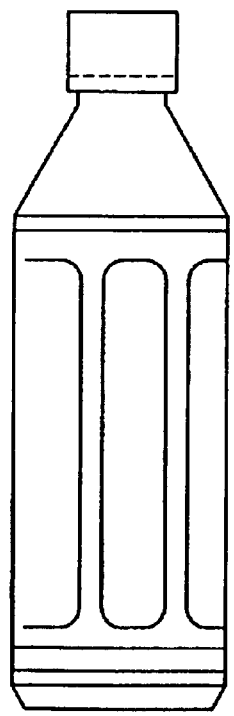
FIGS. 6A and 6B are views showing other examples of the PET bottle.
Figure 6B:
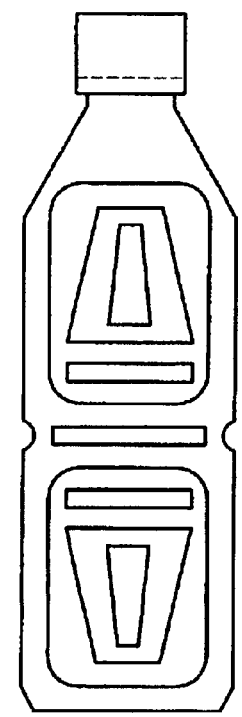

FIG. 5 shows a detection state of the PET bottle 20. The PET bottle 20 is transported through an inspection unit in an upright posture on a transportation unit 25, such as a belt conveyor or a turntable, and goes into a detection state(plan view) as shown in FIG. 4 during the transportation. The PET bottle 20 may be PET bottles as shown in FIGS. 6A and 6B.

Figure 7:
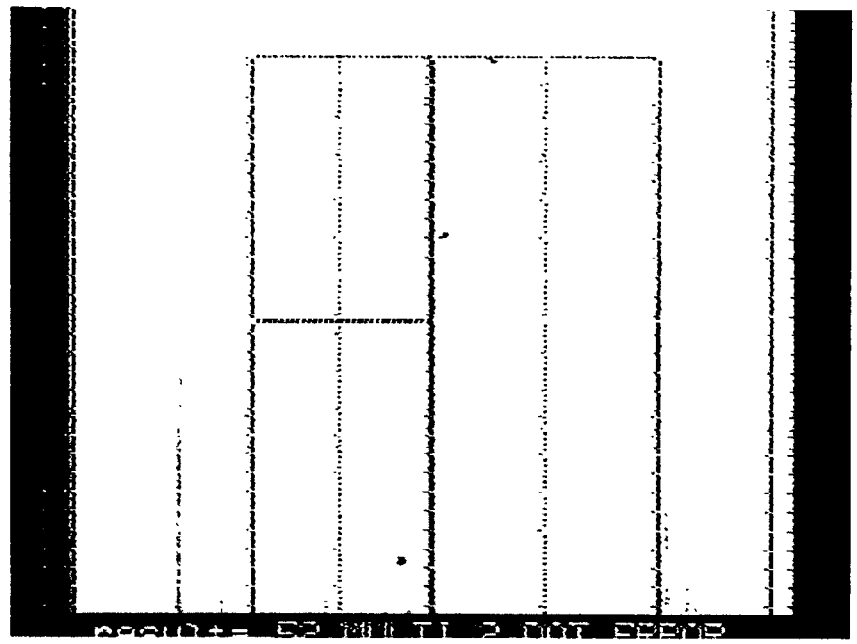
FIG. 7 is a view showing an image as an example of a pictured image(raw data) by the present invention.
Figure 8:
FIG. 8 is a view showing an image as an example of a processed image(binary data) by the present invention.

According to the arrangement described as above, the outside shape line of the PET bottle 20 is removed from an image pictured by the CCD sensor 30, and as a result, image information(raw data) as shown in FIG. 7 is obtained. FIG. 7 shows an image when a transparent PET bottle is filled with a transparent liquid, and a black frame is a virtual line indicating an area for ease of image processing. The image processing unit 31 converts the image information thus obtained into binary data and a binary image as shown in FIG. 8 is obtained, in which a foreign matter alone can be identified clearly. Consequently, the foreign matter judging circuit 32 can judge the presence of a foreign matter in a reliable manner.

When the liquid 21 is a colored liquid, such as coffee, cola or milk, or when the PET bottle 20 is opaque or translucent, infrared light is used as the light source 23 and the light sources 24A and 24B. When the liquid 21 is colored, the foreign matter 22 is invisible from the outside, which makes it difficult to detect the foreign matter 22 by visual inspection or an optical method. However, by using certain infrared light as irradiated light, it is possible to detect a foreign matter that is invisible from the outside. An example case using certain infrared light in inspection for a foreign matter is described in Japanese Patent Application Nos. 2000-357665 and 2001-18055 filed by the applicant of the present application.

To be more specific, an object being inspected is irradiated with infrared light having a wavelength of 750 to 1000 nm from an infrared light source at power in the range from 0.7 mW to 100 W, and transmitted light from the object being inspected is collected by an objective lens and received by the CCD sensor, whereby it is possible to detect a foreign matter. The CCD sensor has wide and high wavelength sensitivity characteristics(ranges of the wavelength and the sensitivity that the photo-receiver can response) covering from blue to near-infrared, thereby having high quantum efficiency in trapping photons. The quantum efficiency of a picture is 2 to 3% at most; however, the quantum efficiency of the CCD sensor is as high as 90%. Also, the CCD sensor is characterized by its large ratio (dynamic range) of the maximum and minimum brightness that can be measured simultaneously and its superior linearity.

It is discovered that, because of these characteristics, the CCD sensor reserves electrons in a packet by exploiting a phenomenon(photoelectric effect) that free electrons are generated when transmitted light impinges on the CCD sensor, so that by merely reading out these electrons sequentially after exposure of a certain period, in case that molecules have high light transmittance like an aqueous solution, it turns a colored or solid black aqueous solution into a transparent aqueous solution. The same can be said in a case where a colored container is filled with a transparent aqueous solution.

Figure 9:
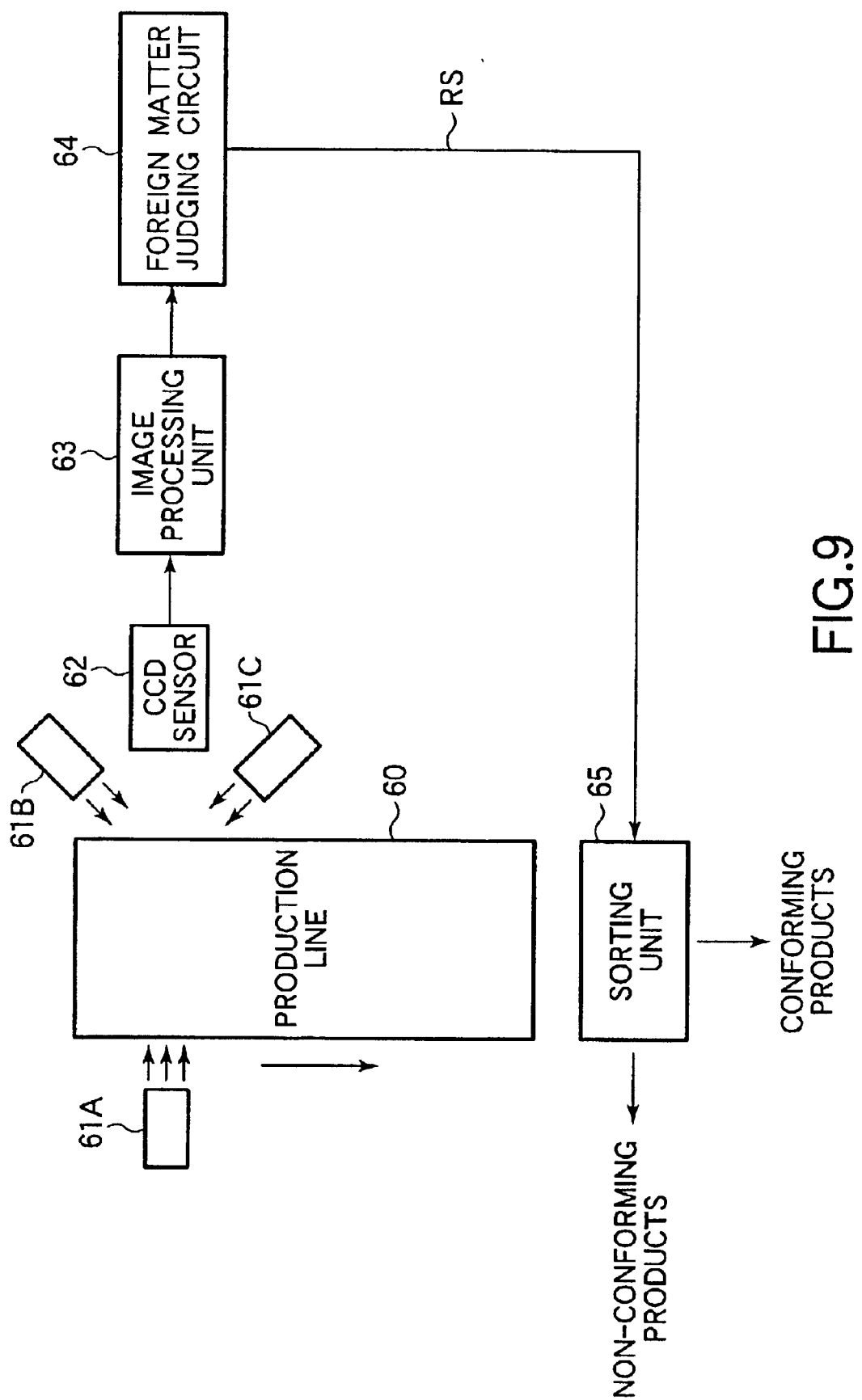
FIG. 9 is a view showing an arrangement of an application example of the present invention.

Next, the following description will describe an example when the invention is applied to a production line with reference to FIG. 9.

Herein, for example, bottles of cola are flowing down on a production line 60, and these bottles of cola are irradiated by a light source 61A provided at the left side of the line to produce transmitted light, and light sources 61B and 61C provided at the right side of the line to produce reflected light. The transmitted light and the reflected light are detected by a CCD sensor 62 provided at the right side of the line. A detection signal from the CCD sensor 62 is subjected to image processing by an image processing unit 63, and a foreign matter judging circuit 64 judges the presence or absence of a foreign matter. Upon judging the presence of a foreign matter, the foreign matter judging circuit 64 outputs a remove signal RS. The production line 60 is provided with a sorting unit 65 for sorting out the bottles of cola, which removes a bottle of cola corresponding to the remove signal RS, thereby sorting out conforming products and non-conforming products. Consequently, it is possible to manufacture and ship only the conforming products.

In the above embodiment, two light sources are employed to produce reflected light; however, four or more light sources may be employed as long as the light quantities are equal in the right and in the left.

As has been described, according to the present invention, the contour or the shape of the object being inspected is removed from an image pictured by the imaging means, so that even when the container is of a complicated shape, only a foreign matter got entered a liquid filled in the container can be identified from a change in intensity caused by the container itself in a reliable manner without being adversely affected by reflection of scattered light from the outside or a bright line, thereby making it possible to detect a minute foreign matter at a high speed and accuracy. Thus, the foreign matters got entered products can be inspected on one hundred percent inspection basis after liquids are filled in containers in a high-speed mass-production line, which makes it possible to enhance reliability and increase yields.

Further, by using a certain infrared light source, even when a bottle or a PET bottle is filled with a colored liquid or a bottle or a PET bottle is colored, not only can a foreign matter be detected in case it has entered the bottle or PET bottle, but also a non-conforming product containing a foreign matter can be removed. Hence, it is possible to remove any foreign matter that may possibly enter just moments before the final product is manufacture by filling a container, such as a bottle and a PET bottle, with a liquid product, thereby further ensuring the product safety.

Obviously many modifications and variations of the invention are possible in the light of the above teachings. It is therefore to be understood that within the scope of the appended claims in the invention may be practiced otherwise than as specifically described.

What is claimed is:

1. An inspecting method for a foreign matter, comprising:
    a step of irradiating an object being inspected that contains a liquid product with light from a first side face thereof;
    a step of irradiating said object being inspected with light given with a tilt from either side of a second side face opposite to said first side face with respect to said object being inspected;
    a step of receiving transmitted light and reflected light from said object being inspected by imaging means provided at said second side face end;
    a step of processing an image signal from said imaging means; and
    a step of detecting a foreign matter [got entered] in said liquid product based on said image processing.

2. An inspecting method for a foreign matter according to claim 1, wherein an angle of said tilt is 30° to 60° with respect to a normal to said first side face of said object being inspected.

3. An inspecting method for a foreign matter according to claim 1, wherein light irradiated from said first side face and light irradiated from either side of said second side face are infrared light having a wavelength of 750 to 1000 nm.

4. An inspecting method for a foreign matter according to claim 3, wherein said infrared light is irradiated at power in a range from 0.7 mW to 100 W both inclusive.

5. An inspecting apparatus for a foreign matter, comprising:
    a first light source for irradiating an object being inspected that contains a liquid product with light from a first side face thereof;
    a plurality of second light sources for irradiating said object being inspected with light given with a tilt from either side of a second side face opposite to said first side face with respect to said object being inspected;
    imaging means, provided at said second side face, for receiving transmitted light and reflected light from said object being inspected; and
    image processing and judging means for detecting a foreign matter [got entered] in said liquid product by processing an image signal from said imaging means.

6. An inspecting apparatus for a foreign matter according to claim 5, wherein said imaging means is a CCD sensor.

7. An inspecting apparatus for a foreign matter according to claim 6, wherein said first light source and said second light sources are infrared light having a wavelength of 750 to 1000 nm.

8. An inspecting apparatus for a foreign matter according to claim 6, wherein the number of said plurality of second light sources is two.

9. An inspecting apparatus for a foreign matter according to claim 7, wherein said first light source and said second light sources have power in a range from 0.7 mW to 100 W both inclusive.

10. An inspecting apparatus for a foreign matter according to claim 5, wherein the number of said plurality of second light sources is two.

* * * * *